United States Patent [19]

Kurkake

[11] Patent Number: 4,774,412
[45] Date of Patent: Sep. 27, 1988

[54] SCINTILLATION CAMERA SYSTEM

[75] Inventor: Tadakazu Kurkake, Ootawara, Japan

[73] Assignee: Kabushiki Kaisha Toshiba, Kawasaki, Japan

[21] Appl. No.: 937,044

[22] Filed: Dec. 2, 1986

[30] Foreign Application Priority Data

Dec. 3, 1985 [JP] Japan ................... 60-272059

[51] Int. Cl.⁴ .............................................. G01T 1/166
[52] U.S. Cl. .................................................. 250/363 S
[58] Field of Search ............... 378/197; 250/363 SC, 250/363 SF

[56] References Cited

U.S. PATENT DOCUMENTS

| | | | |
|---|---|---|---|
| 2,967,939 | 1/1961 | Caha et al. | 250/363 SF |
| 4,216,381 | 8/1980 | Lange | 250/363 SC |
| 4,459,485 | 7/1984 | Span | 250/363 SC |
| 4,645,933 | 2/1987 | Gambini et al. | 250/363 SC |

*Primary Examiner*—Carolyn E. Fields
*Attorney, Agent, or Firm*—Finnegan, Henderson Farabow, Garrett and Dunner

[57] ABSTRACT

A scintillation camera system comprising, a detector, a detector-supporting device, and a support mechanism supporting the device. The support mechanism has first and second pivots set apart at a predetermined distance. The detector is designed to detect the radiation emitted from a patient. The detector-supporting device supports the detector rotatably and can prohibit the detector from rotating. The device has third and fourth pivots set apart at substantially the same distance as the first and second pivots are set apart. A first arm is pivotally connected to the first pivot at its proximal end and is pivotally connected to the third pivot at its distal end. A second arm, which has a length substantially equal to that of the first arm, is pivotally connected to the second pivot at its proximal end and is pivotally connected to the fourth at its distal end. The first and second arms and the four pivots constitute a parallel crank mechanism. Hence, the detector moves vertically, while the detector is orientated in one direction as long as the detector-supporting device prohibits the detector from rotating. When the detector-supporting device releases the detector, the detector can be tilted in any desired angle. The detector-supporting device is relatively light, and the scintillation camera system is therefore light and small.

6 Claims, 5 Drawing Sheets

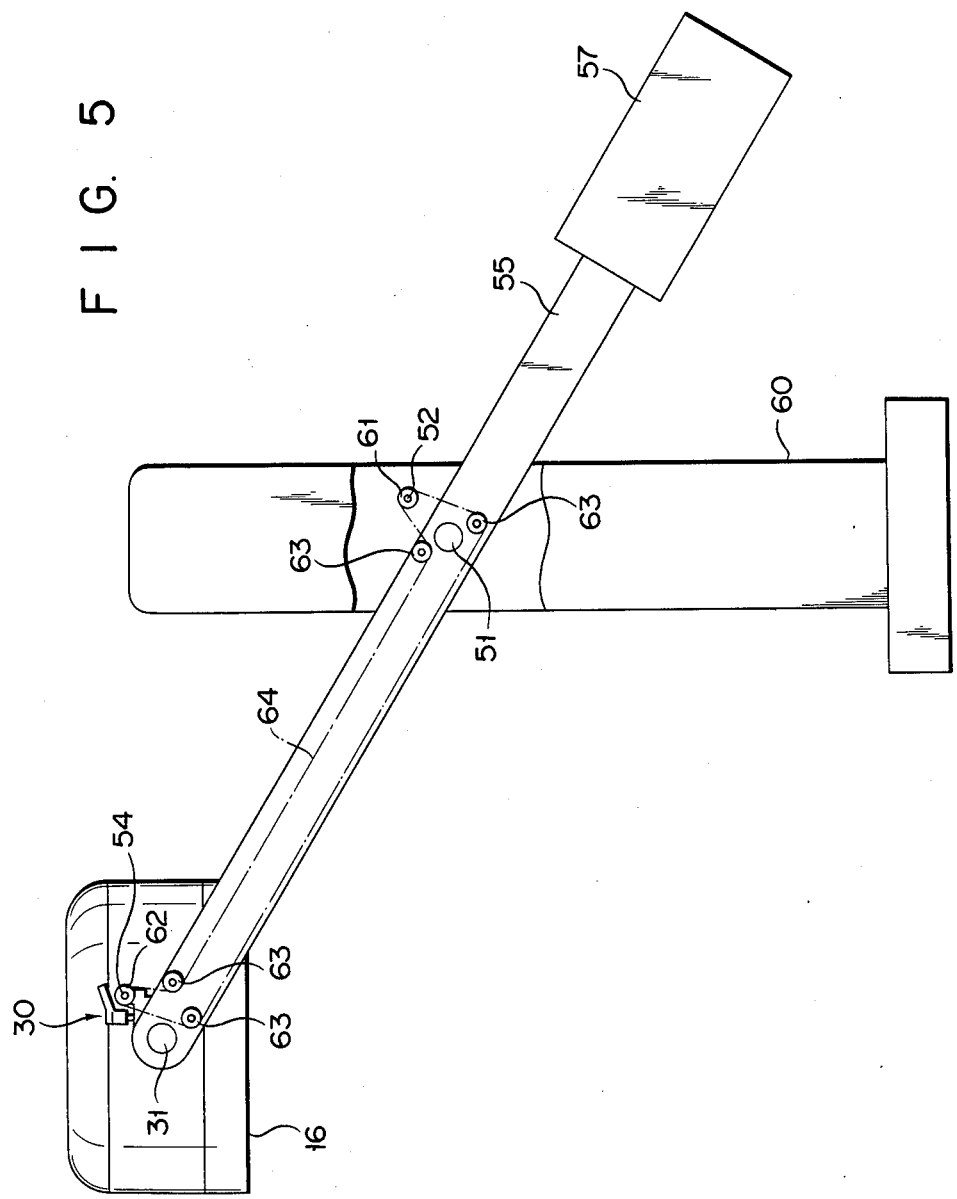

SCINTILLATION CAMERA SYSTEM

BACKGROUND OF THE INVENTION

The present invention relates to a scintillation camera system adapted to emission computed tomography and designed to form an image of a particular area of a patient, and more particularly to a device for supporting the detector used in the system to detect the gamma rays emitted from the patient.

A scintillation camera system has a detector. The detector detects the gamma rays emitted from a patient. The energy of the gamma rays is converted into electrical signals. These electrical signals are supplied to a computer. The computer processes the signals, thereby reconstructing an image of a specified area of the patient.

In the scintillation camera system, a patient lies on a horizontal bed. Scintillation camera systems can be classified into two types. In the first type, the detector is located above the patient. In the second type, the detector is moved around the patient. The system of the first type is adapted mainly to form an image of a particular area of the patient. In this system, the detector is supported at the distal end of an arm, the proximal end of which is pivotally coupled to a stanchion provided beside the patient. The system of the second type is adapted mainly to emission computed tomography. In the system of the second type, the detector is supported at the distal end of an arm, the proximal end of which is pivotally connected to a rotary mechanism which can rotate about the axis of the patient.

In either type of scintillation camera system, the arm is rotated about its proximal end in order to adjust the position of the detector, with respect to the patient. More specifically, the arm is rotated to move the detector vertically. It is desirable that the detector is moved with its gamma ray-receiving surface positioned horizontally and opposing the patient lying on the horizontal bed. To this end, the arm comprises two cranks forming a parallel crank mechanism. Whenever the cranks are rotated, they remain parallel to each other. The detector is, therefore, also moved in parallel to the stanchion (or, to the rotary mechanism). The detector can thereby move in the vertical direction, while the gamma ray-receiving surface remains in a horizontal plane.

After the detector has been set in a predetermined position, it must be tilted by a prescribed angle, in some cases, in order to photograph, for example, the patient's head. U.S. Pat. No. 4,459,485 discloses a device which can incline a detector. This device comprises two cranks forming a parallel crank mechanism, and an auxiliary member having a two-forked distal end. The cranks support the proximal end of the auxiliary member at their respective distal ends. The detector is loosely clamped between the two prongs of the forked distal end of the auxiliary member. The auxiliary member is moved in parallel to a stanchion (or a rotary mechanism) of the type described above. Hence, the detector can move vertically, while its gamma ray-receiving surface remains in a horizontal plane. Further, the detector, which is loosely clamped between the prongs of the auxiliary member, can be tilted when required, whereby the gamma ray-receiving surface can be inclined to the horizontal plane. Even if the gamma ray-receiving surface is tilted by a prescribed angle, the detector can be moved in the vertical direction. As a result, this prior art device can facilitate the positional adjustment of the detector with respect to the patient.

However, since the forked distal end portion of the auxiliary member covers almost half the detector, it is considerably massive and heavy. When the prior art device is incorporated in a scintillation camera system, the system will inevitably be massive and heavy. Consequently, it is difficult to transport and install the scintillation camera system, and also the device supporting the detector must be large.

SUMMARY OF THE INVENTION

It is an object of the present invention to provide a scintillation camera system in which a detector is moved while being kept oriented in one direction, and can be tilted by a prescribed angle when necessary, and which is relatively light in weight and small in size.

According to this invention, there is provided a scintillation camera system which comprises, a detector, a detector-supporting device, and a support mechanism supporting the device. The support mechanism has first and second pivots set apart at a predetermined distance. The detector is provided for detecting the radiation from a patient. The device supports the detector so as to allow the detector to rotate and also to prohibit the detector from rotating. This detector-supporting device has third and fourth pivots set apart at the same distance as the first and second pivots are set apart from each other. The system further comprises first and second arms. The first arm is pivotally connected to the first pivot at its proximal end and is pivotally connected to the third pivot at its distal end. The second arm, which has a length substantially equal to that of the first arm, is pivotally connected to the second pivot at its proximal end, and is pivotally connected to the fourth pivot at its distal end. Hence, the first to fourth pivots and the first and second arms constitute a parallel crank mechanism. When the first arm and the second arm are rotated about the first and second pivots, respectively, thereby to move the detector in the vertical direction, both arms move in parallel to each other. Simultaneously, the line connecting the third and fourth pivots (i.e., the axis of the detector-supporting device) moves in parallel to the line connecting the first and second pivots. Hence, the detector, which is prohibited from rotating by detector-supporting device, is kept orientated in one direction while it is moving. When the detector-supporting device releases the detector and permits the same to rotate, the detector can be tilted by a prescribed angle. Even after the detector has been tilted, it can be moved in the vertical direction. Since the detector-supporting device is light in weight and small in size, the scintillation camera system is relatively light and small.

BRIEF DESCRIPTION OF THE DRAWINGS

FIG. 5 is a side view of a modification of the scintillation camera system shown in FIG. 1.

DETAILED DESCRIPTION OF THE PREFERRED EMBODIMENTS

Figure 1:
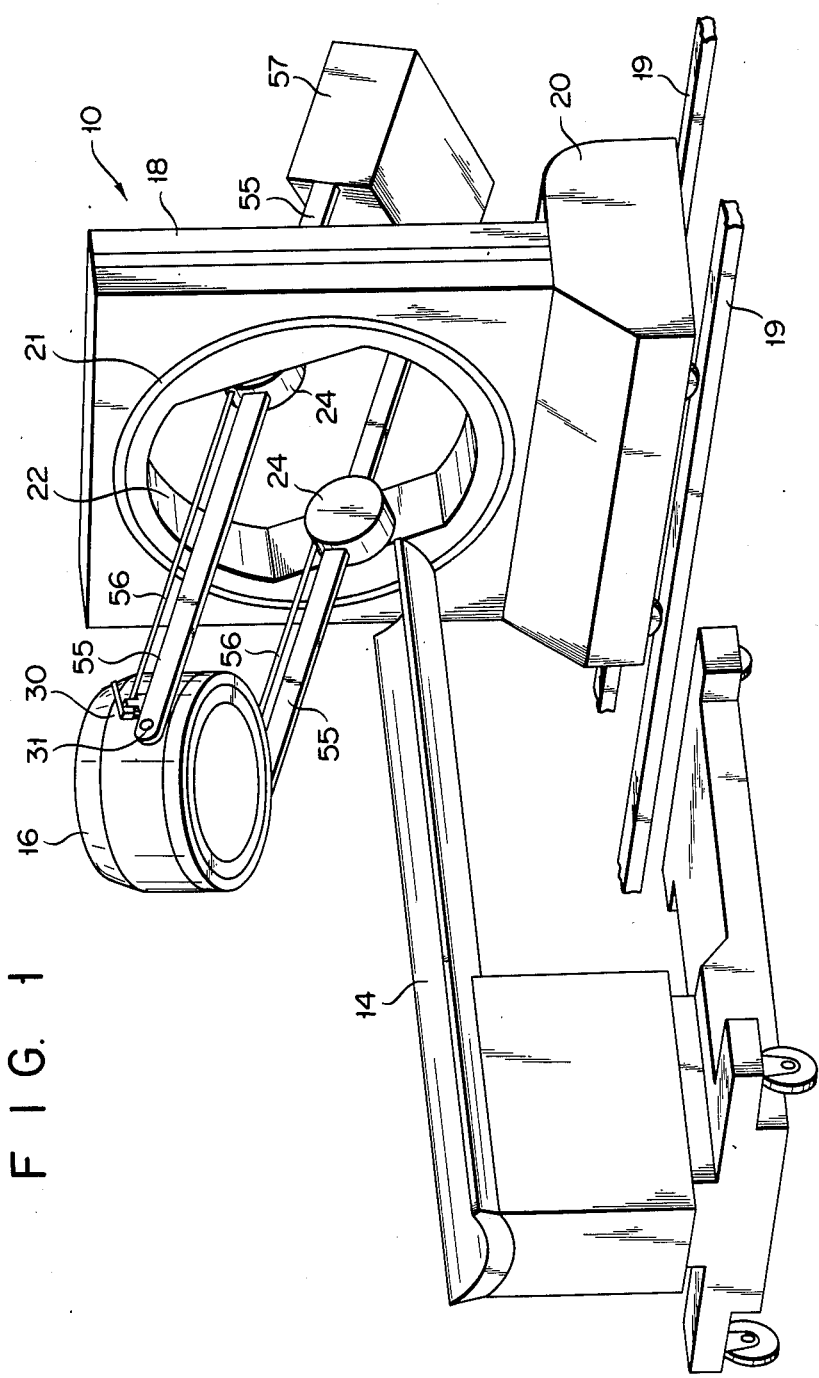
FIG. 1 is a perspective view of a scintillation camera system according to this invention.

As is illustrated in FIG. 1, scintillation camera system 10 of the present invention is provided with detector 16 used to form images of the internal portions of a patient. System 10 is further provided with cantilevered table 14 and rotary mechanism 18. Rotary mechanism 18 is designed to rotate detector 16 around the patient lying on table 14. Two pivots 31 are secured to both sides of detector 16. Pivots 31 allow detector 16 to rotate, but brake device 30 prohibits detector 16 from rotating.

Detector 16 is of the well-known type including scintillation crystals (not shown) and photomultiplier tubes (not shown). An internal dose of radiopharmaceutical compounds, which emit gamma rays, has been administered to the patient. The gamma rays are emitted from the patient. The scintillation crystals receive the gamma rays and convert them into light rays. The photomultiplier tubes detect these light rays and convert them into electrical signals. The electrical signals are supplied to a computer. The computer processes the signals, thereby reconstructing the images of the internal areas of the patient's body.

Figure 2:
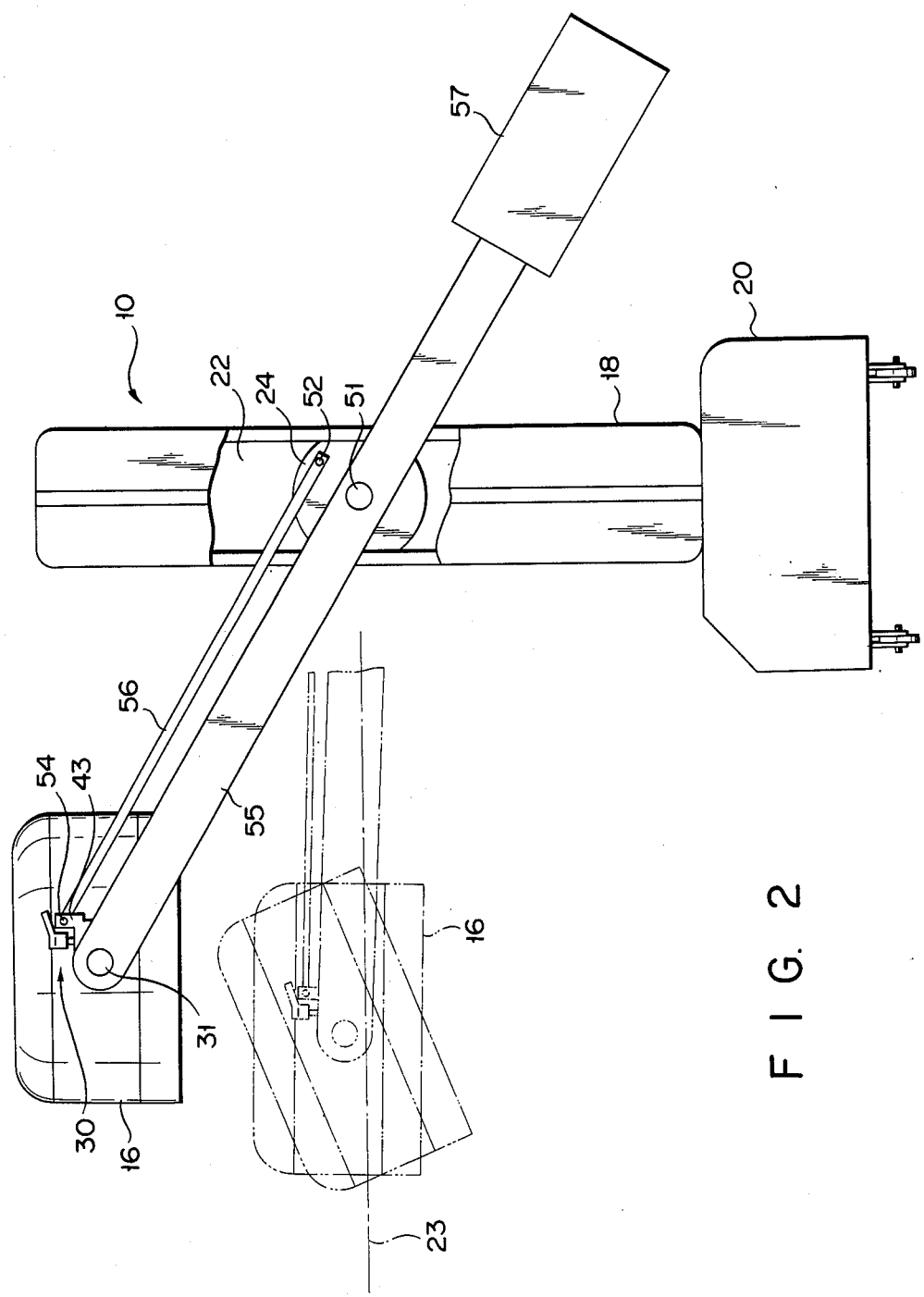
FIG. 2 is a side view of the system shown in FIG. 1.

As is shown in FIGS. 1 and 2, rotary mechanism 18 is mounted on base 20 which can move on rails 19. Mechanism 18 has outer circular ring 21 and inner circular ring 22. Outer ring 21 is fitted in the opening cut in the center part of mechanism 18. Inner ring 22 is set in outer ring 21 but can slide on the inner periphery of ring 21. Inner ring 22 can be rotated about its axis 23 by a motor (not shown) provided within rotary mechanism 18. A pair of arm-supporting members 24 are secured to the inner periphery of inner ring 22. These members 24 are located symmetrically with respect to axis 23 of inner ring 22. Main-arms 55 and sub-arms 56, which will later be described in detail, are supported by each member 24. Detector 16 is coupled to main-arms 55 by brake device 30.

Figure 3:
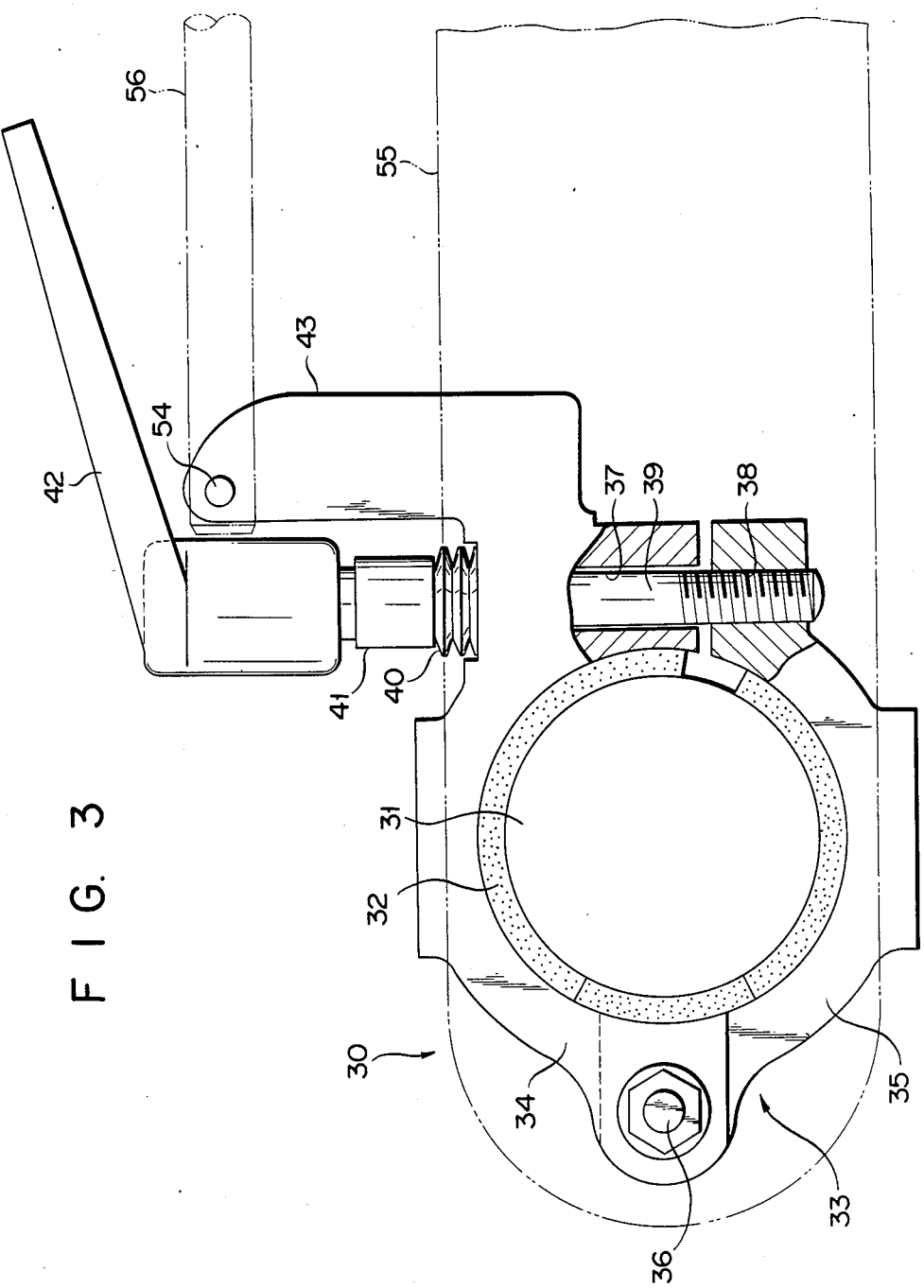
FIG. 3 is a side view of a brake device provided in the system of FIG. 1.
Figure 4:
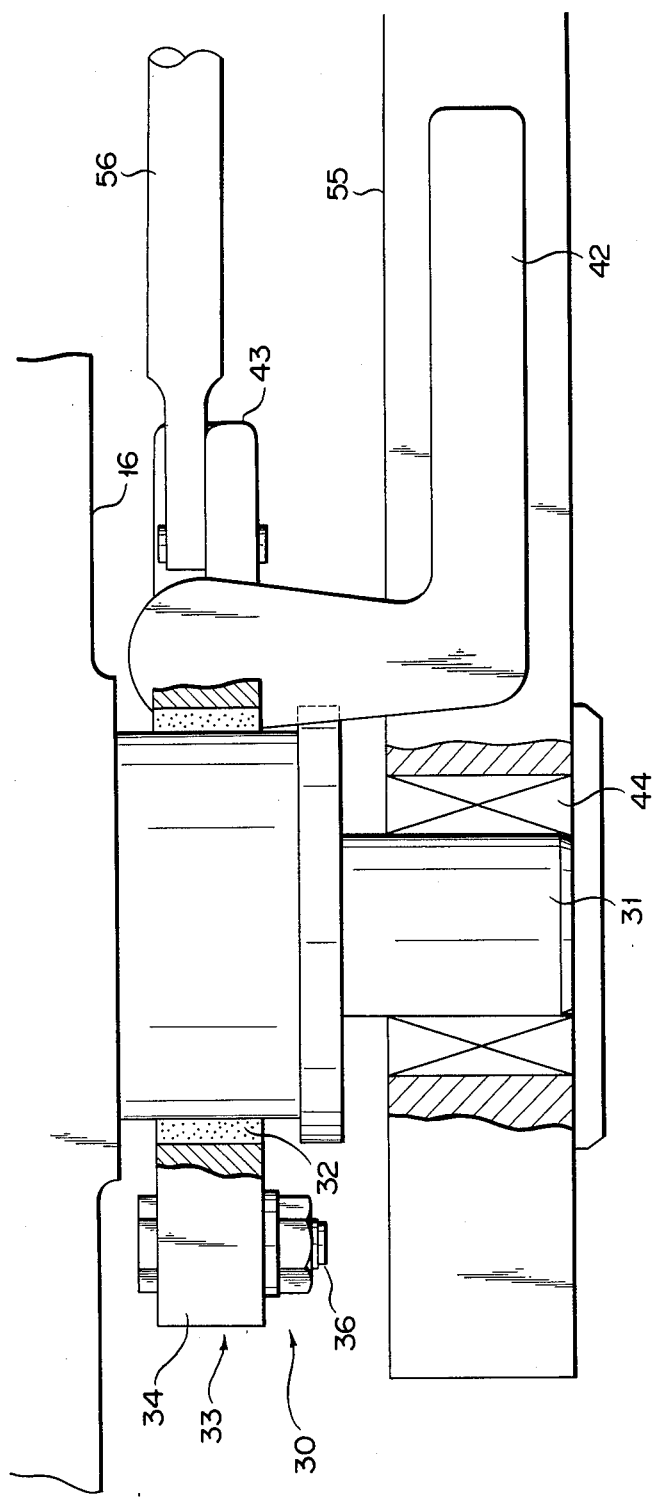
FIG. 4 is a partially sectional, plan view showing the detector used in the system of FIG. 1, and the brake device.

As is illustrated in FIGS. 3 and 4, pivot 31 is secured to one side of detector 16. Brake device 30 is mounted on this pivot 31. Brake device 30 comprises brake shoe 32 and shoe-holding unit 33. Brake shoe 32 is mounted on pivot 31. Shoe-holding unit 33 consists of upper member 34 and lower member 35 which hold brake shoe in place. Upper and lower members 34 and 35 are rotatably connected at one end by bolt 36. They can rotate around the axis of this bolt 36, whereby shoe-holding unit 33 can open or close. Upper member 34 has, at the other end, vertical through-hole 37 whose axis intersects with that of bolt 36. Lower member 35 has, at the other end, vertical screw-hole 38, axially aligned with through-hole 37 of upper member 34. Bolt 39 extends through hole 37 of upper member 34 and is put in screw engagement with hole 38 of lower member 35. Bolt 39 consists of a thin portion and a thick portion. The thin portion is inserted in holes 37 and 38. Washers 40 are mounted on the thin portion of bolt 39, and are interposed between upper member 34 and thick portion 41 of bolt 39. Lever 42 is connected to the upper end of thick portion 41 of bolt 39.

When lever 42 is rotated in one direction about the axis of bolt 39, upper and lower member 34 and 35 are rotated such that shoe-holding unit 33 closes. As a result, brake shoe 32 is pressed onto the periphery of pivot 31, making it impossible for pivot 31 to rotate.

When lever 42 is rotated in the opposite direction around the axis of bolt 39, upper and lower members 34 and 35 are rotated such that shoe-holding unit 33 opens. In this case, brake shoe 32 is released from a tight contact with pivot 31. Hence, pivot 31 can freely rotate relative to brake device 30.

As is shown in FIG. 2, first pivot 51 and second pivot 52 are secured to each arm-supporting member 24. These pivots 51 and 52 are set apart at a predetermined distance. Projection 43 protrudes upwardly from upper member 34 of brake device 30. Horizontal pivot 54 is coupled to projection 43. Pivot 54 is parallel to pivot 31, and its axis is set apart from that of pivot 31 at the same distance as first and second pivots 51 and 52 are set apart.

The distal end of main-arm 55 is rotatably coupled to pivot 31 (the third pivot) by bearing 44. The middle portion of main-arm 55 is rotatably supported by first pivot 51. Counterweight 57 is attached to the proximal end of main-arm 55. With first pivot 51 functioning as a fulcrum, counterweight 57 is sufficiently heavy to balance the arm 55 coupled to detector 16.

The proximal end of sub-arm 56, which has a length equal to that of a portion connecting first and third pivots 51 and 31 of main-arm 55, is rotatably connected to second pivot 52 secured to arm-supporting member 24 which in turn is fastened to the inner periphery of inner circular ring 22. The distal end of sub-arm 56 is rotatably coupled to fourth pivot 54 of brake device 30. The portion connecting first and third pivot 51 and 31 of main-arm 55, sub-arm 56, the line connecting first and second pivots 51 and 52, and the line connecting third and fourth pivots 31 and 54 define a parallelogram. Hence, arms 55 and 56 and pivots 31, 51, 52 and 54 constitute a parallel crank mechanism.

When scintillation camera system 10 is used to achieve emission computed tomography, the position of detector 16 must be adjusted with respect to the patient. That is to say, detector 16 is moved up or down, with its gamma ray-receiving surface kept in a horizontal position. More precisely, either main-arm 55 is rotated around first pivot 51. Either sub-arm 56 is therefore rotated about second pivot 52, moving in parallel to main-arm 55. Simultaneously, the line connecting third and fourth pivots 31 and 54 moves in parallel to the line connecting first and second pivots 51 and 52. In other words, either main-arm 55 is rotated, while brake device 30 is held inclined at the same angle. Hence, as long as brake device 30 prohibits pivot 31 from rotating, detector 16 moves in the vertical direction, with its gamma ray-receiving surface kept in a horizontal position, thus directed in the same direction.

After detector 16 has been positioned, in this way, with respect to the patient, rotary mechanism 18 is operated. Detector 16 is therefore rotated about axis 23 of inner ring 21, and thus around the patient. Emission computed tomography is thus performed.

After detector 16 has been set in a predetermined position with respect to the patient, its gamma ray-receiving surface should be tilted by a prescribed angle in order to reconstruct an image of an internal area of the patient's head. To incline the gamma ray-receiving surface by said angle to a horizontal plane, lever 42 of either brake device 30 is rotated such that shoe-holding unit 33 opens. In other words, the gap between upper and lower members 34 and 35 of unit 33 increases. Brake shoe 32 is released from the tight contact with pivot 31. As a result, detector 16, which is fixed to pivot 31, can be tilted by the prescribed angle. After detector 16 is tilted, lever 42 of either brake device 30 is rotated in the opposite direction, whereby brake device 30 prohibits pivot 31 from rotating. Hence, the gamma ray-receiving surface of detector 16 is held inclined at the prescribed angle to the horizontal plane. Thereafter, this surface remains so inclined even if detector 16 is moved up or down.

A modification of scintillation camera system 10 will now be described with reference to FIG. 5. In this modification, stanchion 60 is used in place of rotary mechanism 18 (FIG. 1). The middle portion of either main-arm 55 is rotatably supported by stanchion 60. Detector 16 and counterweight 57 are coupled to the distal and proximal ends of each main-arm 55, respectively. Pulley 61 is mounted on second pivot 52. Further, pulley 62 is mounted on fourth pivot 54 secured to projection 43 of brake device 30. Moreover, two auxiliary pulleys 63 are rotatably attached to the middle portion of main-arm 55, and two other auxiliary pulleys 63 are rotatably attached to the distal end of main-arm 55. Wire loop 64 is wrapped around pulleys 61, 62 and 63. Hence, as main-arm 55 is rotated about first pivot 51, wire loop 64 achieves the same function as sub-arm 56 does in system 10. That is, due to the use of wire loop 64, the distance between first pivot 51 and third pivot 31 and the distance between second pivot 52 and fourth pivot 54 remain unchanged. Pivots 31, 51, 52 and 54, pulleys 61, 62 and 63, and wire loop 64 constitute a parallel crank mechanism. When main-arm 55 is rotated, wire loop 64 moves at a distance proportionate to the angle of rotation of arm 55. Detector 16 thereby maintains its gamma ray-receiving surface tilted or not tilted to a horizontal plane, as it is moved up and down.

As has been described above, in the present invention, detector 16 can be moved in the vertical direction with its gamms ray-receiving surface orientated in one direction. When necessary, detector 16 can be tilted by a prescribed angle with respect to brake device 30. Further, detector 16 can be moved in the vertical direction, while being kept inclined by the prescribed angle. In short, it is easy to adjust the position of detector 16 with respect to the patient. Moreover, the scintillation camera system of the invention requires no forked auxiliary members, unlike the conventional scintillation camera systems, and can therefore be lighter and smaller than the conventional systems.

The present invention is not limited to the embodiment described above and the modification thereof. In the embodiment, as is shown in FIG. 4, one and the same pivot 31 couples brake device 30 rotatably to main-arm 55 and couples brake device 30 to detector 16. Alternatively, two pivots can be used, one rotatably connecting brake device 30 to main-arm 55, and the other connecting brake device 30 to detector 16.

What is claimed is:

1. A scintillation camera system comprising:
   a first support having a first pivot with a first axis of rotation and a second pivot having a second axis of rotation parallel to said first axis and set apart from said first axis at a first predetermined distance;
   a first arm pivotally connected at one point to said first pivot;
   a second arm pivotally connected at one point to said second pivot;
   a detector for detecting radiation rays emitted from a patient;
   a second support having a third pivot with a third axis of rotation and a fourth pivot having a fourth axis of rotation parallel to said third, second, and first axis of rotation and set apart from said third axis of rotation at said first predetermined distance, said first arm pivotally connected at a second point a second predetermined distance from said first point to said third pivot and said second arm pivotally connected at a second point said second predetermined distance from said first point to said fourth pivot to form a parallel crank, said third pivot being fixed to said detector and comprising an axis of rotation for said detector and said second support including means for selectively preventing rotation of said third pivot relative said second support while permitting rotation of said third pivot relative said first arm, so as to permit rotation of said first and second arms about said first and second pivots while maintaining said detector in a fixed orientation relative said patient.

2. A scintillation camera system according to claim 1, wherein said first support includes a circular ring having a fifth axis of rotation perpendicular to said first and second axes of rotation, and wherein said first and second pivots are secured to said circular ring.

3. A scintillation camera system according to claim 1, wherein said first support comprises a stanchion, and said first and second pivots are secured to one side of said stanchion.

4. A scintillation camera system according to claim 1, wherein said third pivot comprises a shaft, and said means for selectively preventing rotation comprises:
   a brake shoe for rotatably supporting said shaft and for prohibiting at selected times said shaft from rotating relative and said second support;
   a shoe-support unit comprising first and second shoe-holding members holding said brake shoe and pivotally coupled to each other at one end, said first and second shoe-holding members being operable to open to release the shaft of said detector from said brake shoe and to close to make said brake shoe engage the shaft and prevent the shaft from rotating relative said second support; and
   means connected to said shoe-support unit for opening and closing said shoe-support unit.

5. A scintillation camera system according to claim 1, wherein siad first arm has an extension extending from said first pivot and away from said detector, and having a counterweight attached to said extension for balancing said first arm and for facilitating rotation of said first arm about said first pivot through a predetermined range of angles.

6. A scintillation camera system comprising:
   a first support having a first pivot with a first axis of rotation and a second pivot having a second axis of rotation parallel to said first axis and set apart from said first axis at a first predetermined distance;
   a first pulley rotatably mounted on said second pivot;
   an arm pivotally connected at one point to said first pivot;
   a detector for detecting radiation rays emitted from a patient;
   a second support having a third pivot with a third axis of rotation and a fourth pivot having a fourth axis of rotation parallel to said third, second, and first axes of rotation and set apart from said third axis of rotation at said first predetermined distance, said arm pivotally connected at a second point a second predetermined distance from said first pivot to said third pivot;

a second pulley rotatably mounted on said fourth pivot;

means, including a wire loop wrapped around said first and second pulleys, for maintaining the distance between said second and fourth pivots equal to said second predetermined distance upon rotation of said arm about said first pivot;

said third pivot being fixed to said detector and comprising an axis of rotation for said detector and said second support including means for selectively preventing rotation of said third pivot relative said second support while permitting rotation of said third pivot relative said arm, so as to permit rotation of said arm about said first pivot while maintaining said detector in a fixed orientation relative said patient.

* * * * *

UNITED STATES PATENT AND TRADEMARK OFFICE
CERTIFICATE OF CORRECTION

PATENT NO.   :   4,774,412
DATED        :   September 27, 1988
INVENTOR(S)  :   Tadakazu Kurakake It is certified that error appears in the above-identified patent and that said Letters Patent is hereby corrected as shown below:

In the Heading, change "Inventor: Tadakazu Kurkake" to

--Inventor: Tadakazu Kurakake--.

Signed and Sealed this

Sixteenth Day of May, 1989

Attest:

DONALD J. QUIGG

*Attesting Officer*　　　*Commissioner of Patents and Trademarks*